United States Patent [19]

Paciorek et al.

[11] Patent Number: 4,557,869
[45] Date of Patent: Dec. 10, 1985

[54] DIHALO-MONOPHOSPHA-S-TRIAZINES AND THEIR DERIVATIVES

[75] Inventors: Kazimiera J. L. Paciorek, Corona del Mar; Reinhold H. Kratzer, Irvine; David H. Harris, Sierra Madre; Mark E. Smythe, Pasadena; James H. Nakahara, Irvine, all of Calif.

[73] Assignee: The United States of America as represented by the Secretary of the Air Force, Washington, D.C.

[21] Appl. No.: 601,874

[22] Filed: Apr. 19, 1984

[51] Int. Cl.[4] .................... C07C 117/00; C07F 9/26
[52] U.S. Cl. .................... 260/349; 252/49.9; 252/389 A; 252/400 A; 260/543 PN; 260/927 N; 564/13; 568/12
[58] Field of Search ............ 260/349, 543 PN, 927 N; 568/12; 564/13

[56] References Cited

U.S. PATENT DOCUMENTS

| | | | |
|---|---|---|---|
| 2,676,985 | 4/1954 | Husted | 260/501.14 X |
| 3,211,753 | 10/1965 | Paciorek et al. | 260/349 |
| 3,212,844 | 10/1965 | Washburn | 260/349 X |
| 3,242,218 | 3/1966 | Miller | 568/615 |
| 3,320,185 | 5/1967 | Alexander et al. | 260/349 X |
| 3,347,876 | 10/1967 | Sharts | 260/349 |
| 3,358,004 | 12/1967 | Bliss et al. | 260/349 |
| 3,715,378 | 2/1973 | Sianesi et al. | 260/463 |
| 3,962,323 | 6/1976 | Toy et al. | 260/543 P |
| 3,997,595 | 12/1976 | Jung et al. | 260/543 P X |
| 4,166,071 | 8/1979 | Paciorek et al. | 260/551 P |
| 4,215,072 | 7/1980 | Paciorek et al. | 260/551 P |

FOREIGN PATENT DOCUMENTS 1350806  4/1974  United Kingdom .

OTHER PUBLICATIONS

Chem. Abstracts, vol. 80, 70845e, p. 351 (1974).
Brown, J. Polym. Sci., 44, 9 (1960).
Fluck et al, Chem. Ber., 96, 3085 (1963).

Primary Examiner—Joseph P. Brust
Attorney, Agent, or Firm—Donald J. Singer; William J. O'Brien

[57] ABSTRACT

This invention concerns itself with a class of novel dihalo-substituted monophospha-s-triazines as exemplified by the compounds 1-dichlorophospha-3,5-bis(perfluoro-n-heptyl)-2,4,6-triazine and 1-dichlorophospha-3,5-bis[$C_3F_7OCF(CF_3)CF_2OCF(CF_3)$]-2,4,6-triazine, as well as their thio and azido derivatives.

10 Claims, No Drawings

4,557,869

DIHALO-MONOPHOSPHA-S-TRIAZINES AND THEIR DERIVATIVES

STATEMENT OF GOVERNMENT INTEREST

The invention described herein may be manufactured and used by or for the Government for governmental purposes without the payment of any royalty thereon.

BACKGROUND OF THE INVENTION

This invention relates in general to novel halogen-substituted monophospha-s-triazine compounds and to a method for their synthesis. In a more particular manner, this invention concerns itself with a method for synthesizing halo-substituted monophospha-s-triazines by effecting a reaction between a phosphorus pentahalide and a perfluoroalkyl or a perfluoroalkylether imidoylamidine and to novel triazine compounds produced thereby.

The novel compounds of this invention, namely the holo-substituted monophospha-s-triazines, are best represented by 1-dichlorophospha-3,5-bis(perfluoro-n-heptyl)-2,4,6-triazine and 1-dichlorophospha-3,5-bis(perfluoroalkylether)-2,4,6-triazine, as well as their thio and azido derivatives. The holo-substituted monophospha-s-triazines provide a hydrogen-free system amenable for use as antioxidation and anticorrosion additives for perfluorinated lubricating fluids and greases. They are useful also as monomers for incorporation into polymers, the latter due to the presence of two replaceable halogens. Other applications will become readily appreciated and apparent to those skilled in the art.

The present interest in the utilization of perfluoroalkylether type fluids for wide temperature range lubricating applications has created a need for effective antioxidant and anticorrosive additives to permit their functioning in the presence of metals and alloys at elevated temperatures. In oxidizing atmospheres and in the presence of titanium alloys, fluids as represented by Krytox 143AC (a product of E. I. DuPont de Nemours and Company, Wilmington, Del., U.S. Pat. No. 3,242,218) undergo extensive degradation and metal corrosion at temperatures below 288° C. (550° F.). Additives such as the 1-di(thiophenyl)phospha-3,5-bis (perfluoroalkyl)-2,4,6-triazines and the 1-di(thiophenyl)phospha-3,5-bis(-perfluoroalkylether)-2,4,6-triazines prevent fluid degradation and metal corrosion and, due to the presence of sulfur, also enhance the fluids' lubricity.

SUMMARY OF THE INVENTION

The present invention resides in the synthesis of a novel class of monophospha-s-triazines having the following structural formula:

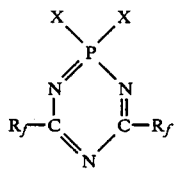

(I)

wherein X is a halogen selected from the group consisting of chlorine and bromine and where $R_f$ is a perfluoroalkyl or perfluoroalkylether group. Examples of the $R_f$ substituent include groups having the formula $C_nF_{2n+1}$, where n is an integer from 1 to 10, inclusive; and $CF_3(OCF_2CF_2)_xOCF_2$, $C_2F_5(OCF_2)_xOCF_2$ and $C_3F_7[OCF-(CF_3)CF_2]_xOCF(CF_3)$, where x is zero or an integer from the 1 to 20, inclusive.

The novel synthesis for preparing the halogen substituted monophospha-s-triazines of this invention comprises the interaction of a perfluorinated imidoylamidine with phosphorus pentahalide in the presence of an acid acceptor. The reaction is generally carried out at temperatures of from about −20° to 30° C.; but, higher or lower temperatures may be utilized.

Accordingly, the primary object of this invention is to provide a series of novel dihalo-substituted monophospha-s-triazine compounds.

Another object of this invention is to provide a novel method for synthesizing dihalo-substituted monophospha-s-triazines by effecting a reaction between a phosphorus pentahalide and a perfluorinated imidoylamidine.

Still another object of this invention is to provide a series of dihalo-substituted monophospha-s-triazines that find particular utility as antioxidant and anticorrosive additives for perfluorinated lubricating fluids.

The above and still other objects and advantages of the present invention will become more readily apparent upon consideration of the following detailed disclosure thereof.

DESCRIPTION OF THE PREFERRED EMBODIMENTS

In accordance with this invention, it has been found that the above-noted objects can be achieved by effecting a reaction between a solvent mixture of phosporus pentahalide and a perfluoroalkyl or perfluoroalkylether imidoylamidine within an inert atmosphere at temperatures and for periods of time sufficient to achieve the synthesis of the novel dihalo-substituted monophospha-s-triazine compounds of this invention.

Previously known monophospha-s-triazines, such as those disclosed in U.S. Pat. No. 4,166,071 to Paciorek et al, were substituted on the phosphorus ring atom by aryl groups and thus were not amenable to transformations into other types of compounds as is possible with the compounds of the present invention. In the compounds of this invention, the halogen groups, identified as X, can be replaced by $N_3$, SR, or OR resulting in novel compositions. Examples of R include $C_6H_5$ and $R'—C_6H_4$, where R′ is an aromatic, alkyl, perfluoroalkyl or perfluoroalkylether moiety; and perfluoroaryl, such as $C_6F_5$ and $R_f'—C_6F_4$ where $R_f'$ is a perfluoroalkyl or perfluoroalkylether group.

The general synthesis contemplated by this invention in synthesizing the dihalo-monophopha-s-triazines is best illustrated by the following equation

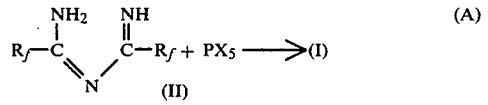

(A)

In the foregoing equation, $R_f$ is defined as above while X is chlorine or bromine. As shown by the equation, the phosphorus pentahalide is reacted with the perfluoroalkyl or perfluoroalkyletherimidoylamidine (II), giving the monophospha-s-triazine (I). The reaction is conducted in mixed solvents such as, e.g., tetrachloroethane and Freon-113 at temperatures ranging from −20° to +30° C. in the presence of an acid acceptor, such as triethylamine, to promote hydrogen chloride elimination. The reaction period is carried out for a period of time sufficient to effect the reaction and usually ranges from 24-72 hours, although longer or shorter periods can be used. The reaction is carried out in an inert atmosphere, e.g., under nitrogen, helium, or argon. In general, equimolar amounts of reactants are used, although it is often preferred to employ an excess of the phosphorus pentahalide reactant.

The substitution of the halogen X in the dihalo-monophospha-s-triazine (I) by another group is carried out using either an alkali metal salt of the substituent or having an acid acceptor present. Thus, in substitution of the halogen by the thio-group, a solution of the dihalo-monophospha-s-triazine is reacted with thiophenol in a solvent such as tetrahydrofuran at temperatures ranging from about 0° to 50° C. in the presence of triethylamine. The product formed is the thiophenyl derivative (III):

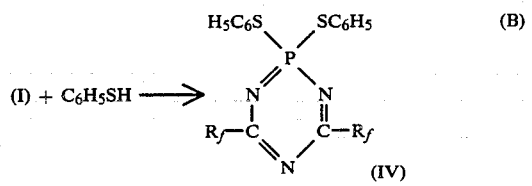

In a similar manner using lithium azide, the diazido triazine (IV) is formed from I:

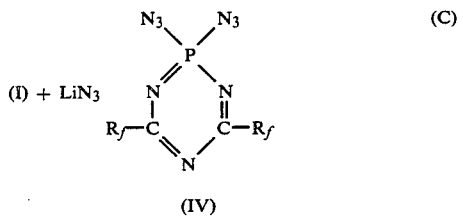

In equations (B) and (C) above, the $R_f$ substituent is defined as in equation (A) and formula (I).

The materials that are used in preparing the triazine products are known compounds that are described in the literature. For example, the perfluoroalkyl and perfluoroalkyletherimidoylamidines are disclosed in French Pat. No. 2,166,498 (1973).

A more complete understanding of the invention can be obtained by referring to the following illustrative examples which are not intended, however, to be unduly limitative of the invention.

EXAMPLE I

Under nitrogen by-pass, a solution of N'-(perfluorooctanoylimidoyl)-perfluorooctanoylamidine (14.40 g, 17.84 mmol) and triethylamine (5.45 g, 53.66 mmol) in Freon-113 (65 ml) was added to a stirred solution of phosphorus pentachloride (4.50 g, 21.61 mmol) in tetrachloroethane (80 ml) at 0° C. over a period of 2 hours. Stirring at 0° C. was continued for an additional hour, followed by 16 hours at room temperature. After addition of Freon-113 (50 ml), the precipitated triethylamine hydrochloride (6.35 g, 86% yield) was filtered off in an inert atmosphere enclosure. The solvents were then removed in vacuo, initially at room temperature, then at 50° C., to leave a yellow oil. Distillation in vacuo gave 1-dichlorophospha-3,5-bis(perfluoro-n-heptyl)-2,4,6-triazine (9.81 g, 61% yield), mp 30°-31° C., bp 80°-84°C./0.001 mm Hg.

Analysis calculated for $C_{16}F_{+}N_3Cl_2P$: C, 21.21; F, 62.91; N, 4.64; Cl, 7.83; P, 3.42; MW, 906.02. Found: C, 21.27; F, 62.55; N, 4.79; Cl, 7.59; P, 3.41; MW, 910.

EXAMPLE II

Under nitrogen by-pass, to a stirred solution of phosphorus pentachloride (2.15 g, 10.32 mmol) in tetrachloroethane (60 ml) at 0° C., was added a solution of the imidoylamidine, $C_3F_7OCF(CF_3)CF_2OCF(CF_3)C(=NH)-N=C(NH_2)CF(CF_3)OCF_2-CF(CF_3)OC_3F_7$ (10.02 g, 10.32 mmol), and triethylamine (3.64 g, 35.97 mmol) in Freon-113 (30 ml), over a period of 1 hour. Stirring at 0° C. was continued for an additional 30 minutes followed by 66 hours at room temperature. The bulk of the solvents was removed in vacuo, followed by addition of Freon-113 (60 ml) to precipitate triethylamine hydrochloride (4.45 g, 100%). Distillation in vacuo of the filtrate afforded 1-dichlorophospha-3,5-bis[$C_3F_7OCF(CF_3)CF_2OCF(CF_3)$]-2,4,6-triazine (4.91 g, 44.5 yield), bp 73°-74° C./0.001 mm Hg.

Analysis calculated for $C_{18}F_{34}Cl_2N_3O_4P$: C, 20.20; F, 60.37; Cl, 6.63; N, 3.93; O, 5.98; P, 2.89; MW, 1070.04. Found C, 20.64; F, 57.47; Cl, 6.39; N, 4.32; P, 2.82; MW, 1090.

EXAMPLE III

In an inert atmosphere enclosure, a solution of triethylamine (0.335 g, 3.31 mmol) and thiophenol (0.4 g, 3.63 mmol) in tetrahydrofuran (10 ml) was added to a stirred solution of 1-dichlorophospha-3,5-bis(perfluoro-n-heptyl)-2,4,6,triazane (1.50 g, 1.66 mmol) in tetrahydrofuran (10 ml) over a period of 30 minutes. Immediate formation of a white precipitate and a yellow solution was observed. After addition, the reaction mixture was stirred at room temperature for 65 hours; subsequent filtration gave triethylamine hydrochloride (0.44 g, 96% yield) and a yellow filtrate. The residue obtained on removal of solvents in vacuo was redissolved in a minimum of Freon-113 (2 ml) and passed through a 1.0×3.0 cm column of neutral Woelm alumina; a pale yellow solid resulted. A combination of recrystallizations from hot hexane and pentane, as well as sublimitation (100°-120° C., 0.001 mm Hg, 2 hours) afforded almost colorless crystals of 1-di(thiophenyl)phospha-3,5-bis(perfluoro-n-heptyl)-2,4,6-triazine (1.25 g, 71% yield), mp 65.5°-67° C.

Analysis calculated for $C_{28}H_{10}F_{30}N_3S_2P$: C, 31.92; H, 0.96; F, 54.10; N, 3.99; P, 2.94; MW, 1053.46. Found: C, 32.19; H, 1.12 F, 52.26; N, 3.68; P, 3.01; MW, 1080.

EXAMPLE IV

In an inert atmosphere enclosure, a solution of triethylamine (0.33 g, 3.26 mmol) and thiophenol (0.40 g, 3.61 mmol) in tetrahydrofuran (13 ml) was added to a stirred solution of 1-dichlorophospha-3,5-bis[$C_3F_7OCF(CF_3)CF_2OCF(CF_3)$]-2,4,6-triazine (1.76 g, 1.64 mmol) in tetrahydrofuran (25 ml) over a period of 30 minutes. Immediate formation of a white precipitate and yellow solution was observed. After addition, the reaction mixture was stirred at room temperature for 17 hours; subsequent filtration gave triethylamine hydrochloride (0.41 g, 91% yield) and a yellow filtrate. The residue obtained on removal of solvents in vacuo was redissolved in Freon-113 and passed through a 0.8×8 cm column of neutral Woelm alumina; a yellow liquid resulted which, on heating in vacuo (6 hr at 75° C.), afforded some white sublimate of diphenyldisulfide. The residual yellow liquid was pure 1-di(thiophenyl)- phospha-3,5-bis[C$_3$F$_7$OCF(CF$_3$)CF$_2$OCF(CF$_3$)]-2,4,6-triazine (1.25 g, 62% yield).

Analysis calculated for C$_{30}$H$_{10}$F$_{34}$N$_3$O$_4$S$_2$P: C, 29.60; H, 0.83; F, 53.06; N, 3.45; S, 5.27; P, 2.54; MW, 1217.48. Found C, 29.29; H, 1.16; F, 50.90; N, 3.61; S, 5.29; P, 2.38; MW, 1230.

The antioxidative and anticorrosive action of 1-di(thiophenyl)-phospha-3,5-bis[(C$_3$F$_7$OCF(CF$_3$)CF$_2$OCF(CF$_3$)]-2,4,6-triazine is illustrated by a test given below carried out at elevated temperature in oxygen in the presence of a Ti(4Al,4Mn) alloy using Krytox 143A fluid, a product of E. I. DuPont de Nemours and Company, Wilmington, Del. A control run in the absence of the additive was conducted under otherwise identical conditions. In the test, a coupon of Ti(4Al,4Mn) alloy was suspended in a sealed tube containing either a fluid alone or fluid plus the additive. The exposure duration and temperature are denoted in the table below. The action of the additive is clearly evident from the drastically reduced amount of volatiles formed, oxygen consumed, and the unchanged appearance of the metal coupon.

TABLE

| Fluid type | Amt g | Additive wt % | Temp °C. | Exposure hr | Oxygen consumed mg | mg/g[1] | Total product formed mg | mg/g[2] |
|---|---|---|---|---|---|---|---|---|
| Krytox 143AC | 4.79 | none | 316 | 24 | 75 | 15.7 | 758.7 | 158.4 |
| Krytox 143AC | 4.78 | 1% | 316 | 24 | 7.9 | 1.7 | 7.7 | 1.6 |

[1]Oxygen consumed in mg/g fluid employed.
[2]Products formed in mg/g fluid employed.

EXAMPLE V

In an inert atmosphere enclosure, to a slurry of lithium azide (0.40 g, 8.17 mmol) in acetonitrile (10 ml) was added a mixture of 1-dichlorophospha-3,5-bis(perfluoro-n-heptyl)-2,4,6-triazine (2.00 g, 2.21 mmol) in acetonitrile (25 ml). The phosphatriazine was only partially soluble in the acetonitrile. After stirring at room temperature for 65 hours, a white precipitate (0.32 g) of lithium chloride and unreacted lithium azide was filtered off. The pale yellow filtrate gave, on removal of solvents, a pale yellow oil which was redissolved in Freon-113 and purified by passing through a 1.0×4.0 cm column of neutral Woelm alumina. Distillation gave 1-diazidophospha-3,5-bis(perfluoro-n-heptyl)-2,4,6-triazine as a colorless liquid which solidified on cooling (1.30 g, 64% yield), bp 85°–90° C./0.001 mm Hg; mp 35°–36° C.

Analysis calculated for C$_{16}$F$_{30}$N$_9$P: C, 20.91; F, 62.01; N, 13.71; P, 3.37; MW, 919.16. Found: C, 20.37; F, 62.49; N, 12.99; P, 3.33; MW, 970.

While the invention has been described with particularity in reference to specific embodiments thereof, it is to be understood that the disclosure of the present invention is for the purpose of illustration only and is not intended to limit the invention in any way, the scope of which is defined by the appended claims.

What is claimed is:

1. The compound 1-dichlorophospha-3,5-bis(perfluoro-n-heptyl)-2,4,6-triazine.

2. A method for synthesizing 1-dichlorophospha-3,5-bis(perfluoro-n-hepty)-2,4,6 triazine which comprises the steps of:

(I) forming a reaction mixture consisting essentially of (A) phosphorous pentachloride and (B) a solution of N'-(perfluorooctanoylimidoyl)-perfluorooctanoylamidine and triethylamine;

(II) stirring said reaction mixture at a temperature of about 0° C. for a period of time of about 3 hours followed by continued stirring at room temperature for a period of time of about 16 hours to effect a reaction therebetween; and (III) separating the resultant reaction product.

3. The compound 1-dichlorophospha-3,5-bis[C$_3$F$_7$OCF(CF$_3$)CF$_2$OCF(CF$_3$)]-2,4,6 triazine.

4. A method for synthesizing 1-dichlorophospha-3,5-bis[C$_3$F$_7$OCF(CF$_3$)CF$_2$OCF(CF$_3$)]2,4,6-triazine which comprises the steps of:

(I) forming a reaction mixture consisting essentially of (A) phosphorous pentachloride and (B) a solution of an imidoylamidine having the structural formula C$_3$F$_7$OCF(CF$_3$)CF$_2$OCF(CF$_3$)C(=NH)—N=C(NH$_2$)—CF(CF$_3$)—OCF$_2$CF(CF$_3$)OC$_3$F$_7$ and triethylamine;

(II) stirring said reaction mixture at a temperature of about 0° C. for a period of time of about 1.5 hours followed by continued stirring at room temperature for a period of time of about 66 hours to effect a reaction therebetween; and (III) separating the resultant reaction product.

5. The compound 1-di(thiophenyl)phospha-3,5-bis(perfluor-n-heptyl)-2,4,6-triazine.

6. A method for synthesizing 1-di(thiophenyl)phospha-3,5-bis(perfluoro-n-heptyl)-2,4,6-triazine which comprises the steps of:

(I) forming a reaction mixture consisting essentially of (A) a solution of 1-dichlorophospha-3,5-bis(perfluoro-n-hepty)-2,4,6-triazine and (B) a solution of thiophenol and triethylamine;

(II) stirring said reaction mixture at room temperature for about 65 hours to effect a reaction therebetween; and (III) separating the resultant reaction product.

7. The compound 1-di(thiophenyl)phospha-3,5-bis[C$_3$F$_7$OCF(CF$_3$)CF$_2$OCF(CF$_3$)]-2,4,6-triazine.

8. A method for synthesizing 1-di(thiophenyl)phospha-3,5-bis[C$_3$F$_7$OCF(CF$_3$)CF$_2$OCF(CF$_3$)-2,4,6-triazine which comprises the steps of:

(I) forming a reaction mixture consisting essentially of (A) a solution of 1-dichlorophospha-3,5-bis[C$_3$F$_7$OCF(CF$_3$)CF$_2$OCF(CF$_3$)]-2,4,6-triazine and (B) a solution of thiophenol and triethylamine;

(II) stirring said reaction mixture at room temperature for about 17 hours to effect a reaction therebetween; and (III) separating the resultant reaction product.

9. The compound 1-diaidophospha-3,5-bis-(perfluoro-n-heptyl)2,4,6-triazine.

10. A method for synthesizing 1-diazidophospha-3,5-bis(perfluoro-n-hepty)-2,4,6-triazine which comprises the steps of:

(a) forming a reaction mixture consisting essentially of
  (1) 1-dichlorophospha-3,5-bis(perfluoro-n-hepty)-2,4,6-triazine and (2) a slurry of lithium azide in acetonitrile;
(b) stirring said reaction mixture at room temperature for about 65 hours to effect a reaction therebetween; and
(c) separating the resultant reaction product.